United States Patent
Neubauer

[11] Patent Number: 6,039,937
[45] Date of Patent: Mar. 21, 2000

[54] RAZOR CONDITIONER

[76] Inventor: Edwin P. Neubauer, 642 Cress Creek Sq., Crystal Lake, Ill. 60014

[21] Appl. No.: 08/886,910

[22] Filed: Jul. 2, 1997

[51] Int. Cl.[7] .................................. A61K 7/15; A61K 7/26
[52] U.S. Cl. ............................. 424/73; 424/74; 424/195.1
[58] Field of Search ............................ 424/73, 74, 195.1; 514/937

[56] References Cited

U.S. PATENT DOCUMENTS

| | | | |
|---|---|---|---|
| 3,887,702 | 6/1975 | Baldwin | 424/61 |
| 4,505,902 | 3/1985 | Millard | 424/195.1 |
| 4,525,344 | 6/1985 | Tutsky | 424/73 |
| 5,007,533 | 4/1991 | Purohit | 206/208 |
| 5,251,752 | 10/1993 | Purohit | 206/352 |
| 5,252,331 | 10/1993 | Curtis et al. | 424/401 |
| 5,332,516 | 7/1994 | Stephens | 252/54 |
| 5,345,680 | 9/1994 | Vreeland et al. | 30/41 |
| 5,362,488 | 11/1994 | Sibley et al. | 424/78.05 |

*Primary Examiner*—Thurman K. Page
*Assistant Examiner*—James M. Spear
*Attorney, Agent, or Firm*—Thomas R. Vigil

[57] ABSTRACT

The liquid composition for treating razors and razor blades comprises, as a main ingredient, an oil, such as a vegetable oil, combined with a small amount of vitamin E (tocopherol acetate). The oil is present in an amount of 80–99.8% by volume and can be almond or canola oil. The vitamin E is present in the amount of 0.01–4% by volume. Other materials such as an anti-friction compound and/or Tea Tree Oil can be included in small amounts in the liquid composition. The method of treatment is to store the razor or razor blade in the liquid composition between uses thereof to enhance the useful life of the razor or razor blade.

16 Claims, No Drawings

RAZOR CONDITIONER

BACKGROUND OF THE INVENTION

1. Field of the Invention

The present invention relates to a liquid preparation or composition which has been found to be highly effective in extending the life of a razor blade when the razor blade is stored in the liquid composition between uses of the razor blade in shaving. The major ingredients of the liquid composition are oil, vitamin E (tocopherol acetate) and, if desired, an anti-friction liquid, typically comprising:

1. 75%–98% by volume chlorinated paraffin with a chlorine content between 35% and 75%;
2. 2%–5% by volume rust inhibitor selected from the group consisting of compounds which inhibit the corrosion of chlorinated paraffins phenols and polyphenols;
3. up to 0.02% by volume of an antimicrobial compound.

2. Description of the Related Art Including Information Disclosed under 37 CFR §§ 1.97–1.99.

Heretofore, various analogous and non-analogous liquid preparations for razors and for lubricating metal parts have been proposed. Several examples of such liquid preparations are disclosed in the following U.S. Patents:

| U.S. Pat. No. | Patentee |
|---|---|
| 4,505,902 | Millard |
| 5,007,533 | Purohit |
| 5,251,752 | Purohit |
| 5,252,331 | Curtis et al. |
| 5,332,516 | Stephens |
| 5,345,680 | Vreeland et al. |
| 5,362,488 | Sibley et al. |

SUMMARY OF THE INVENTION

According to the present invention there is provided a liquid composition for treating razors and razor blades comprising, as a main ingredient, an oil, such as a vegetable oil, combined with a small amount of vitamin E (tocopherol acetate). The oil is present in an amount of 80–99.8% by volume and can be almond or canola oil. The vitamin E is present in the amount of 0.01–4% by volume. Other materials such as an anti-friction compound and/or Tea Tree Oil can be included in small amounts in the liquid composition.

The method of treatment is to store the razor or razor blade in the liquid composition between uses thereof to enhance the useful life of the razor or razor blade.

DESCRIPTION OF THE PREFERRED EMBODIMENT(S)

"Conventional Wisdom" suggests that the practical, comfortable service life of a razor blade is determined by corrosion damage to the shaving edge. When the cutting edge of the razor becomes jagged and pitted by corrosion, the shaver's face is irritated and nicked by the razor and the razor is discarded in favor of a new one.

Research has shown, however, that the razor's cutting edge is not destroyed by corrosion as one normally thinks of corrosion, i.e., by chemically pitting or the actual destroying the metal. Rather, in normal shaving procedures, there is a build-up of hard, sharp salt crystals that are the residue of the dissolved minerals in the water. These salt crystals are deposited on the razor surface as water droplets on the razor's surface evaporate. There are salts dissolved in both hard and soft water, and as long as the razor is allowed to "air dry", a salt built-up will take place.

Typically today, a razor is discarded after 10 shaves because the shave is no longer comfortable. In test studies, razor blades used for 10 and 15 "normal" shaves were examined at high magnification. The cutting edges of the metal blades were not pitted or otherwise attacked by chemical action as one would expect to see based upon "conventional wisdom". Instead, jagged clumps were deposited along the shaving edge and on the surface of the blades. The cutting edges of these used razors, when compared with new, unused blades, looked as though they were still capable of cutting facial hair cleanly.

Why do razor blades have such a short, useful service life if the cutting edge is still capable of cleanly cutting facial hair? It is strongly believed that the deposited clumps are responsible for the facial irritation and nicking that end the razor's useful service life.

If these clumps are responsible for shortening a razor's service life, what steps might be taken to eliminate or to prevent them? Both of these approaches were examined.

One way of removing "calcium deposits" in coffee brewers and tea pots is to use household vinegar to dissolve them. Then, why not use vinegar to remove the clumps before shaving? Or, why not store the razor in a vinegar solution? This was tried; and indeed shaves as good as with new blades were experienced for as long as 20 shaves. However, the vinegar attacked the metal of the razor handle, so this approach was abandoned.

An old, old practice of coating metal parts with grease or oil to protect them from rusting, or corroding, is still practiced today. When the coating is removed, the metal parts are as bright and clean as when they were coated. When razor blades are new, there is a thin film of oil on them that is left from the manufacturing process. Although this may not be the intent, this film helps keep the blades free from rust during packaging and storage until they are displayed at retail and then purchased. When a razor blade is used in shaving, this oil film is destroyed.

When the shaving procedure is completed, the razor is rinsed and normally allowed to dry in the air, air dry. As stated above, there are minerals dissolved in tap water. If the water droplets on the razor blades were displaced by another oil film or coating, there would not be any dissolved salts to be deposited on the blades.

Rather than just coating the razor blades with oil, it was deemed more convenient to store the razor in oil between shaves.

The first oil tried was baby oil which is basically mineral oil with fragrance added. When razors stored in baby oil were used for shaving, the shaves' comfort level increased, and the razors were used longer comfortably than razors used in a "normal" manner. In addition to shaves that did not irritate the skin, the razor glided across the skin easily.

Even though shaving became more pleasant, there was still some facial discomfort after rinsing with water following the shave. Since experience teaches that vitamin E soothes facial dryness, vitamin E was added to the baby oil. When vitamin E, in the form of tocopherol acetate, was added to the baby oil, the feel of the shave improved dramatically. That is, the razor glided across the facial skin much more easily, and the skin felt even better than shaving with a new razor. Shaving was no longer a chore to be endured but it actually became a pleasant experience.

While the elimination of salt deposits on the razor blade surfaces alone improved the comfort level of shaving, there was still the matter of nicks and cuts that is detrimental to a good shave.

The razor was then rinsed in distilled water and ethyl alcohol after shaving to see if eliminating the source of the salt deposits would by itself lead to quality shaves. During these shaves, the skin was not irritated by abrasion from salt deposits, and the shaves were comfortable. The shaving experience was similar to the initial vinegar trials. However, after several shaves, the razor began inflicting nicks to the facial skin, and the razor did not seem to glide across the skin as easily as when the oil treatment was used. Even when care was exercised in drawing the razor across the skin there were nicks.

The thin film of oil on a new razor is removed during the shaving process, and during subsequent shaves friction may become a factor. Water is a lubricant and shaving creams and gels also lubricate the shave. However, after the thin oil film from manufacturing is removed, the lubrication of water and shaving lather becomes ineffective; and friction between the razor blade and the skin is enough to cause nicks of the skin.

It is believed, although not scientifically proven, that cuts and nicks are caused when friction between the razor and the skin becomes large enough that the razor blade pushes skin ahead of the cutting edge rather than gliding evenly over the skin's surface. The shave becomes a series of jerky slip-slides where the cutting edge of the razor sometimes catches a piece of skin before it can pass under the razor, and a nick, or cut, is inflicted.

Some faces seem to be more susceptible to nicks and cuts than others. The difference may be that some skins secrete more natural oil, and this natural oil lubricates the passage of the razor across the skin.

In addition to vitamin E, other additions were made to the razor treatment. The one which remained in the final mixture was an anti-friction additive which had been used in experimental friction testing. This additive, described in U.S. Pat. No. 5,332,516, reduces frictional drag by bonding to a metal surface and holding a very, very thin oil film in place. Since a razor is rinsed with hot water during shaving, it was believed that the lubricating affect of the razor treatment might be lessened as the hot water would rinse away some of the treatment oil. The lubricating value of the treatment oil would be enhanced if it were more tightly held onto the razor surface. Therefore, the anti-friction additive became part of the treatment mix as lubrication insurance.

Such anti-friction additive typically includes:
1. 75%–98% by volume chlorinated paraffin with a chlorine content between 35% and 75%;
2. 2%–5% by volume rust inhibitor selected from the group consisting of compounds which inhibit the corrosion of chlorinated paraffins phenols and polyphenols;
3. up to 0.02% by volume of an antimicrobial compound.

It will be understood that the exact components can very so long as they fall within the teachings of U.S. Pat. No. 5,332,516, the disclosure of which is incorporated herein by reference.

Two objections to mineral oil were that an "oily feel" was left on the face after shaving and that beard stubble did not rinse from the sink basin readily. Vegetable oils were tried next as the primary material for coating the razor. Canola oil, an extract of rapeseed, is considered to be a natural replacement for mineral oil because it has good lubricity, it is readily available, it is low cost, and it has good emolliency, a plus for facial use. The "oily feel" disappeared, or was dramatically reduced, and the rinsing problem also seemed to disappear. Most importantly, the comfort of shaving remained.

Why are razor blades thrown away after only 10 shaves? The most obvious reason to be given would be that the shave is not comfortable. An attempt at defining "shaving comfort" is set forth below.

When a razor is new, the surfaces and cutting edge have a very light oil coating and are "clean" of any sharp, extraneous material. The manufacturing process has produced a polished surface and sharp cutting edge. The new blade(s) slide across the face and cut the hair easily. Generally, a "like new" shave is a desirable event.

As stated above, when razors are allowed to air dry between shaves, the dissolved salts in tap water are deposited on the surface and along the cutting edge. The effect of these deposits is to generate the equivalent of a very fine grade of sandpaper on the razor surface. The face is subjected to abrasion be this sandpaper and tiny scratches result which sting. As the deposits become more numerous and larger with subsequent "air drying", the severity of abrasion increases until the person shaving will no longer tolerate it. Also, as the abrasion increases, the facial skin stings after shaving when the small scratches are exposed to air.

Abrasion and cuts may be the major source of shaving discomfort; therefore, if these are eliminated from the shave, shaving would then be comfortable. Thus, let's define a comfortable shave as "a shave with clean, smooth passage of the razor across the skin, with the face being free of irritation."

Razor blade manufacturers have tried to make shaving "smoother" by adding strips of material on the cartridge body intended to "lubricate" the shave. These strips may reduce the friction between the face and the cartridge body material, but do they affect the friction between the face and the razor blade surface? Probably not. If there is friction between the cartridge body and the face, does it contribute to facial discomfort from shaving? Probably not by the definition given above.

Razor blade manufacturers have tried to reduce the corrosion of the razor blade by coating the blade. This coating may increase the corrosion resistance of the blade metal, but does this coating keep the blade surface free of salt deposits?

Razor blade manufacturers have tried various design approaches to give the shaver closer shaves. While these various design may allow the blade to cut the facial hair closer to, or maybe even below, the skin level, does this increase the useful life of the razor and does the shave become any more comfortable? Probably not.

Water conditions vary across the country from naturally soft to chemically softened to untreated well water. All of these various water conditions have a certain dissolved salt content The total dissolved salt content of the water used by a shaver will determine the build-up rate of salt deposits on a razor's surface. Under an idyllic situation where rain water or distilled water could be used for washing the face and shaving, the build-up of salts on a razor's surface would be eliminated. This would reduce or eliminate irritation to the shaver's face by the salt build-up, the facial comfort of the shave would improve, but the shaver might still experience nicks and cuts. It is believed that this is because the blade surfaces would not be coated with a lubricant to reduce the friction between the facial skin and the razor's surface.

Based upon the above examination of the problem, it is believed that any disposable razor manufactured today, whether a disposable cartridge or a disposable razor, will give the shaver a superior shave when it is given a treatment that preserves the cleanliness of the razor's surfaces and decreases the frictional drag of the razor across the shaver's face. It is also believed that once a razor blade is in the hands of the person who is about to shave, shaving comfort is dependent solely upon the treatment and care given the razor by the shaving owner. Further, it is believed that lesser costly razors will shave as comfortably as more costly ones.

During one test, the head of a disposable Gillette brand razor was used by the lead tester. This was done because the tester liked the feel of the razor handle he had been using, and the head of the disposable razor could be removed from the disposable handle and it fit the owner's handle. Also, buying disposable razors was less costly than buying throw away cartridges.

What is the useful life of a razor? In two separate tests, the lead tester used a razor for 77 shaves in one trial, and one for 100 shaves in another trial. In each instance the razor being evaluated gave comfortable shaves throughout the test period. It is believed that the comfort level was at least that of a razor after three or four shaves using conventional practices. It is also believed that 100 shaves is not the limit a razor might be used; these tests were halted so that the blades could be examined and it was found under a microscope that the blade appeared substantially the same as an unused blade.

In summary the liquid treatment according to the teachings of the present invention included a liquid composition comprising one of the following five compositions:

1. 80–99.8% by volume of oil
   0.1–10% by volume of vitamin E
   0–10% by volume of anti friction compound preferably comprising:
   (a) 75%–98% by volume chlorinated paraffin with a chlorine content between 35% and 75%;
   (b) 2%–5% by volume rust inhibitor selected from the group consisting of compounds which inhibit the corrosion of chlorinated paraffins phenols and polyphenols; and,
   (c) up to 0.02% by volume of an antimicrobial compound.

2. 95–99.9% by volume of mineral oil
   0.1–5% by volume of vitamin E.

3. 95–99% by volume of vegetable oil
   0.5–4% by volume of vitamin E
   0.5–4% by volume of anti friction compound, preferably comprising:.
   (a) 75%–98% by volume chlorinated paraffin with a chlorine content between 35% and 75%;
   (b) 2%–5% by volume rust inhibitor selected from the group consisting of compounds which inhibit the corrosion of chlorinated paraffins phenols and polyphenols; and,
   (c) up to 0.02% by volume of an antimicrobial compound 4. 95–99.5% by volume of almond oil
   0.5–4% by volume of vitamin E
   0–1% by volume of Tea Tree Oil.

5. 94–96.8% by volume of canola oil (rapeseed extract)
   0.1–0.5% by volume of vitamin E
   0.1–0.25% Tea Tree Oil
   3–5% by volume of anti friction compound, preferably comprising:
   (a) 75%–98% by volume chlorinated paraffin with a chlorine content between 35% and 75%;
   (b) 2%–5% by volume rust inhibitor selected from the group consisting of compounds which inhibit the corrosion of chlorinated paraffins phenols and polyphenols; and,
   (c) up to 0.02% by volume of an antimicrobial compound.

and had the following advantages:
   Eliminated nicks and cuts.
   Eliminated facial burn or irritation.
   Extended the useful life of a razor.
   Changed a daily chore into a pleasant task.

If desired a fragrance, such as, for example, menthol or peppermint oil, can be added in a small mount to the liquid composition.

From the foregoing description, it will be apparent that the liquid composition and its method of use or treatment of the present invention have a number of advantages, some of which have been described above and others of which are inherent in the invention. Also it will be understood that modifications can be made to the liquid composition described above without departing from the teachings of the present invention. Accordingly, the scope of the invention is only to be limited as necessitated by the accompanying claims.

I claim:

1. A liquid composition for treating razors and razor blades comprising an oil, consisting essentially of a vegetable oil in an amount from approximately 80% up to approximately 99.99% by volume, combined with vitamin E (tocopherol acetate) in an amount from approximately 0.01% up to approximately 4% by volume.

2. The liquid composition of claim 1 wherein said vegetable oil is almond oil.

3. A liquid composition for treating razors and razor blades comprising, as a main ingredient, canola oil (rapeseed extract) in an amount from approximately 80% up to approximately 99.99% by volume combined with vitamin E (tocopherol acetate) in an amount from approximately 0.01% up to approximately 4% by volume.

4. The liquid composition of claim 1 further including an anti friction compound in an amount of 0.1–10% by volume.

5. The liquid composition of claim 4 wherein said antifriction compound is present in an amount of 0.01–5% by volume.

6. A liquid composition for treating razors and razor blades comprising, as a main ingredient, an oil in an amount from approximately 80% up to approximately 99.99% by volume combined with vitamin E (tocopherol acetate) in an amount from approximately 0.01% up to approximately 4% by volume and an anti-friction compound in an amount of approximately 0.1–10% by volume comprising:
   (a) 75%–98% by volume chlorinated paraffin with a chlorine content between 35% and 75%;
   (b) 2%–5% by volume rust inhibitor selected from the group consisting of compounds which inhibit the corrosion of chlorinated paraffins phenols and polyphenols; and,
   (c) up to 0.02% by volume of an antimicrobial compound.

7. A liquid composition for treating razors and razor blades comprising, as a main ingredient, an oil in an amount from approximately 80% up to approximately 99.99% by volume combined with vitamin E (tocopherol acetate) in an amount from approximately 0.01% up to approximately 4% by volume and Tea Tree Oil in an amount from approximately 0.01% up to approximately 1.0% by volume.

8. A liquid composition for treating razors and razor blades comprising, as a main ingredient, an oil in an amount from approximately 80% up to approximately 99.99% by volume combined with vitamin E (tocopherol acetate) in an amount from approximately 0.01% up to approximately 4% by volume and menthol.

9. A liquid composition for treating razors and razor blades comprising, as a main ingredient, an oil in an amount from approximately 80% up to approximately 99.99% by volume combined with vitamin E (tocopherol acetate) in an amount from approximately 0.01% up to approximately 4% by volume and peppermint oil.

10. A method for treating a razor or razor blade to enhance its useful life comprising the step of storing the razor or razor blade in a liquid composition comprising, as a main ingredient, an oil combined in an amount from approximately 80% up to approximately 99.99% by volume with vitamin E (tocopherol acetate) in an amount from approximately 0.01% up to approximately 4% by volume.

11. A method of treating a razor or razor blade to enhance its useful life comprising the step of storing the razor or razor blade in a liquid composition comprising, as a main ingredient, an oil in an amount from approximately 80% up to approximately 99.99% by volume combined with vitamin E (tocopherol acetate) in an amount of approximately 0.01% up to approximately 0.05% by volume.

12. The liquid composition of claim 3 wherein said vitamin E is present in an amount of approximately 0.01–0.05% by volume.

13. The liquid composition of claim 6 wherein said vitamin E is present in an amount of approximately 0.01–0.05% by volume.

14. The liquid composition of claim 7 wherein said vitamin E is present in an amount of approximately 0.01–0.05% by volume.

15. The liquid composition of claim 8 wherein said vitamin E is present in an amount of approximately 0.01–0.05% by volume.

16. The liquid composition of claim 9 wherein said vitamin E is present in an amount of approximately 0.01–0.05% by volume.

* * * * *